(12) United States Patent
Wachs et al.

(10) Patent No.: US 6,331,503 B1
(45) Date of Patent: Dec. 18, 2001

(54) IN-SITU FORMATION OF METAL-MOLYBDATE CATALYSTS

(75) Inventors: Israel E. Wachs, Bridgewater, NJ (US); Laura E. Briand, Buenos Aires (AR)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 09/287,021

(22) Filed: Apr. 6, 1999

Related U.S. Application Data
(60) Provisional application No. 60/081,950, filed on Apr. 15, 1998.

(51) Int. Cl.[7] .............................. B01J 23/00; B01J 23/40; B01J 23/42; B01J 23/58; B01J 23/60
(52) U.S. Cl. .................. 502/305; 502/306; 502/307; 502/311; 502/313; 502/314; 502/315; 502/316; 502/317; 502/318; 502/319; 502/321; 502/325; 502/326; 502/328; 502/329; 502/330; 502/331; 502/337; 502/338; 502/340; 502/343; 502/344; 502/345; 502/353; 502/38; 502/39
(58) Field of Search .................................. 502/305, 306, 502/307, 311, 313, 314, 316, 317, 319, 325, 321, 326, 338, 340, 344, 353, 355, 38, 39, 315, 318, 328–331, 337, 343, 345

(56) References Cited
U.S. PATENT DOCUMENTS

| | | | |
|---|---|---|---|
| 1,913,405 | * 6/1933 | Meharg . | |
| 2,491,695 | * 12/1949 | Stiles ...................................... | 260/603 |
| 2,812,309 | * 11/1957 | Allyn et al. ........................... | 252/470 |
| 3,152,997 | * 10/1964 | Natta et al. ........................... | 252/470 |
| 3,408,309 | * 10/1968 | Gessner ................................. | 252/470 |
| 3,415,886 | * 12/1968 | McClellan ............................. | 260/603 |
| 3,716,497 | * 2/1973 | Courty ................................... | 252/470 |
| 3,846,341 | * 11/1974 | Courty ................................... | 252/462 |
| 3,975,302 | * 8/1976 | Courty et al. ..................... | 252/455 R |
| 3,983,073 | * 9/1976 | Trifiró et al. ......................... | 252/470 |
| 3,987,107 | * 10/1976 | McClellan et al. ............ | 260/603 HF |
| 4,024,074 | * 5/1977 | Cairati et al. ........................ | 252/470 |
| 4,141,861 | * 2/1979 | Courty et al. ........................ | 252/462 |
| 4,181,629 | * 1/1980 | Cairati et al. ........................ | 252/458 |
| 4,208,353 | * 6/1980 | Webster et al. ...................... | 568/472 |
| 4,212,766 | * 7/1980 | Brazdil et al. ....................... | 252/432 |
| 4,306,089 | * 12/1981 | Webster et al. ...................... | 568/472 |
| 4,331,567 | * 5/1982 | Canavesi et al. .................... | 252/470 |
| 4,343,954 | * 8/1982 | Hoene .................................. | 568/473 |
| 4,829,042 | * 5/1989 | Cavalli et al. ........................... | 2/316 |
| 5,217,936 | * 6/1993 | Sarup et al. ......................... | 502/241 |

\* cited by examiner

Primary Examiner—Steven P. Griffin
Assistant Examiner—Cam N. Nguyen
(74) Attorney, Agent, or Firm—Banner & Witcoff, Ltd.

(57) ABSTRACT

The method of the present invention involves the in situ formation of metal-molybdate catalyst particles active for methanol oxidation to formaldehyde, with iron as an example, the catalyst is made by mixing particulate forms of $Fe_2O_3$ and $MoO_3$ which form an active $Fe_2(MoO_4)_3/MoO_3$ component inside the reactor during methanol oxidation.

7 Claims, 1 Drawing Sheet

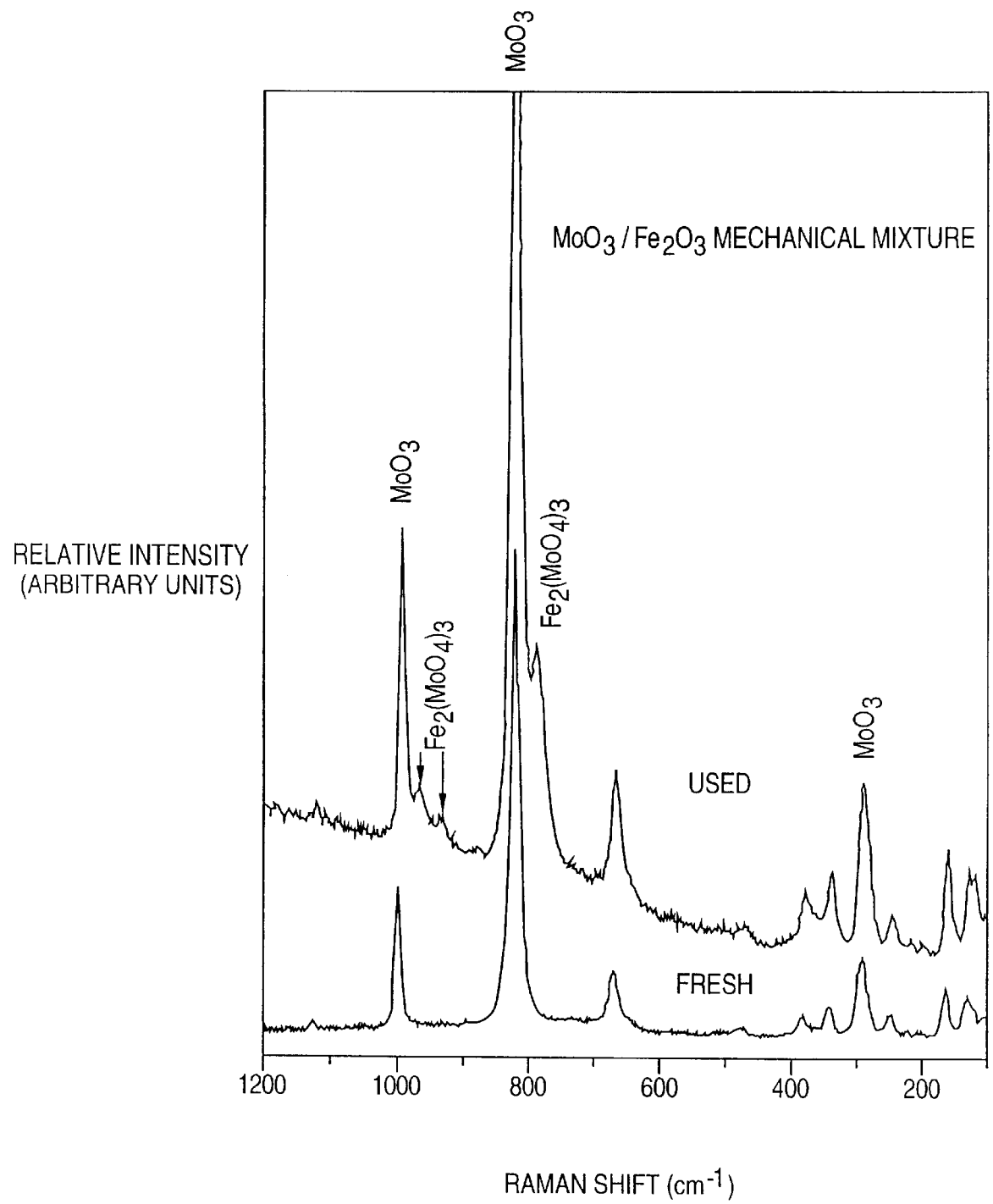

US 6,331,503 B1

IN-SITU FORMATION OF METAL-MOLYBDATE CATALYSTS

This application claims the priority benefits from the U.S. provisional application Ser. No. 60/081,950 filed Apr. 15, 1998.

FIELD OF THE INVENTION

The present invention is directed to a novel methodology for an in situ preparation of metal-molybdate catalysts that are useful for methanol oxidation to formaldehyde.

BACKGROUND OF THE INVENTION

Iron-molybdate catalysts have been manufactured from the coprecipitation of aqueous solutions of $FeCl_3$ and ammonium heptamolybdate. Both of these reagents are expensive and significant amounts of water are required in the commercial manufacture of the iron-molybdate catalysts in accordance with prior manufacturing methods. In addition, during the calcination step required to form the active $Fe_2(MoO_4)_3$ and $MoO_3$ components, significant amounts of pollutants, such as nitrous oxides ($NO_x$), ammonia ($NH_3$) and hydrochloric acid (HCl) are formed.

Thus, the synthesis of iron-molybdate catalysts prior to the present invention has a number of significant problems. In view of these significant problems, there is a need for new methods of formation for these catalysts. More specifically, there is a need for methods of manufacture of iron-molybdate catalysts that involve more common and less expensive reagents, do not require water, and reduce the formation of pollutants. The present invention fulfills all of these needs. These and other benefits of the present invention are described below.

BRIEF SUMMARY OF THE INVENTION

It has now been discovered that in situ formation of metal-molybdate catalysts can be achieved by beginning the methanol conversion process over a physical mixture comprising: (a) a particulate source of catalytically active metal oxide and (b) a source of molybdenum oxide such as molybdenum trioxide ($MoO_3$). During the course of the methanol conversion reaction, catalytically active metal-molybdate/($MoO_3$) forms in situ and without the use of water.

For the formation of the preferred iron-molybdate catalysts, a combination of (a) a particulate source of iron oxide such as powdered forms of ferric oxide ($Fe_2O_3$), coprecipitated iron molybdate ($Fe_2(MoO_4)_3$), or other metal oxide such as NiO; and (b) a source of molybdenum oxide such as molybdenum trioxide ($MoO_3$) are loaded into a methanol conversion zone. During the course of the methanol conversion reaction at typical conversion conditions, catalytically active metal molybdate (e.g. ($Fe_2(MoO_4)_3$)/ ($MoO_3$)) forms in situ and without the use of water.

Metal-molybdate catalysts formed by the present invention and the resulting methanol conversion process are comparable to metal-molybdate catalysts formed via the more expensive and polluting manufacturing methods of the prior art. These and other advantages will be readily recognized by those skilled in the art.

BRIEF DESCRIPTION OF THE FIGURES

FIG. 1 is a spectra of a Raman analysis showing the formation of iron-molybdate from a physical mixture of molybdenum trioxide and ferric oxide contacted with methanol and oxygen under conventional methanol oxidation conversion conditions.

DETAILED DESCRIPTION OF THE PREFERRED EMBODIMENT

The present invention is directed to the formation of compositions within a fixed bed reactor that are catalytically active for the oxidative conversion of alcohols to their corresponding aldehydes. Notably, the catalysts are formed in situ from a physical mixture of readily available or easily synthesized solids that are the source of a metal oxide and molybdenum oxide. While the precise mechanism is not exactly known, it is believed that catalytically active molybdenum trioxide ($MoO_3$) is formed in the course of the conversion reaction at the conversion conditions, is transferred among the solid surfaces within the conversion bed, and thereby forms the present catalytically active composition. Notably, the present composition exhibits a higher conversion and selectivity for aldehyde production than each individual particulate type catalyst added to the conversion bed.

Suitable sources of catalytically active metal oxide include iron, lead, cadmium, zinc, bismuth, sodium, manganese, gadolinium, magnesium, copper, cobalt, tellurium, aluminum, chromium, nickel, and combinations thereof. Exemplary forms of catalytically active compositions that are formed by this process include $Fe_2(MoO_4)_3$/ $MoO_3$, $PbMoO_4$, $CaMoO_4$, $Bi_2Mo_2O_9$, $Bi_3(FeO_4)(MoO_4)_3$ and other Bi-Mo-O family members, $Na_2MoO_4$, $Na_2Mo_2O_7$, $MnMoO_4$, $Gd_2(MoO_4)_3$, $MgMoO_4$, $CuMoO_4$, $CoMoO_4$, $Te_2MoO_7$, $Al_2(MoO_4)_3$, $Cr_2(MoO_4)_3$, $NiMoO_4$, and $ZnMoO_4$.

The invention is conveniently described with reference to the formation of the preferred iron-molybdate catalysts although it will be understood that the formation can be applied to the other metals identified above.

In the preferred method of the present invention, mixtures of inexpensive particulate forms of iron oxide and molybdenum oxide are useful for the oxidative conversion of methanol to formaldehyde under conventional methanol conversion conditions. Suitable conversion conditions generally include a temperature within the range from about 150°–500° C., preferably 250°–400° C., in a flowing stream of gas containing methanol, oxygen, and a carrier gas that is inert to the reaction. Useful gas streams contain these reactants in a molar ratio generally suitable for synthesis of formaldehyde, such as in a molar ratio of methanol/oxygen that is within the range of 1–4. A particularly useful stream contains 6 moles methanol to 13 moles oxygen to 81 moles of helium. Gas phase compositions suitable for synthesis of formaldehyde from methanol over metal molybdate catalysts are well known to those skilled in the art.

Particularly preferred catalysts according to the invention include a particulate mixture of: (a) $Fe_2O_3$ (21.4 $m^2/g$) and $MoO_3$(5.0 $m^2/g$); or (b) $Fe_2(MoO_4)_3$(9.6$m^2/g$) and $MoO_3$ (5.0 $m^2/g$), in the form of finely divided, free flowing, intimately admixed powders that are initially loaded into a fixed catalyst bed and used to catalyze the oxidative conversion of methanol to formaldehyde at conventional conversion conditions. During the course of that process, a catalytically active $Fe_2(MoO_4)_3/MoO_3$ component is formed in situ in the catalyst bed.

FIG. 1 illustrates the Raman analysis of the mixture $MoO_3$ and $Fe_2O_3$ before (fresh catalyst) and after (used catalyst) the catalytic test at high methanol conversion. The Raman spectrum of the fresh sample shows the characteristic signals of $MoO_3$ at 996, 819 and 667 $cm^{-1}$. Iron oxide gives a very weak signal that is not detectable at the scale of FIG. 1.

After the reaction, new Raman bands at approximately 968 and 781 cm$^{-1}$ that belong to $Fe_2(MoO_4)_3$ along with those of molybdenum trioxide ($MoO_3$) are detected. The analysis clearly demonstrates that the active phase $Fe_2(MoO_4)_3/MoO_3$ was formed during the methanol reaction.

EXAMPLES

Molybdenum trioxide ($MoO_3$), ferric oxide ($Fe_2O_3$), nickel oxide (NiO) and coprecipitated iron-molybdate ($Fe_2(MoO_4)_3$) and various mixtures and combinations thereof, were screened for conversion of methanol and selectivity toward formaldehyde production. The iron-molybdate catalysts were made by coprecipitating an ammonium molybdate (e.g., $(NH_4)Mo_7O_{24} \cdot 4H_2O$)) with iron nitrate solution at appropriate temperature and pH for precipitation. The precipitated solids are then washed, dried, and calcined to make particulate catalysts for the oxidative conversion of methanol to formaldehyde. The "turnover frequency" ("TOF") is the reaction rate divided by the number of surface active sites per surface area of catalyst. The number of active sites was determined by methanol chemisorption at 100° C.

The results of the screening tests are shown in the attached Tables I and II, and the following conclusions can be drawn:
1. By comparing the results obtained with the pure compounds $MoO_3$, $Fe_2(MoO_4)_3$, $Fe_2O_3$, and NiO and those belonging to the mixtures with an excess of molybdenum trioxide (Mo/Fe>1.5), it can be concluded that an excess of $MoO_3$ improves the catalytic activity and selectivity in the methanol oxidation process.
2. The same results of activity and selectivity are obtained by using a mixture of $Fe_2(MoO_4)_3/MoO_3$ prepared by the traditional coprecipitation method and a mixture obtained by simple mechanical mixtures of $Fe_2(MoO_4)_3$ and $MoO_3$, or $Fe_2O_3$ and $MoO_3$.
3. The catalytic activity and selectivity in the methanol oxidation process obtained with the mechanical mixtures is comparable with a well known industrial catalyst provided by Perstorp Polyols (Toledo, Ohio) with product designation KH-26L.

In Table III, the results of catalytic activity at high methanol conversion of the mechanical mixtures compared with the industrial catalyst described above are shown. This data was taken in a conventional flow reactor, operating at 380° C., with approximately 100 mg of catalyst in the form of powder, under a stream of 54 sccm of methanol/oxygen/helium in the molar ratio of 6/13/81. The results show that the mechanical mixtures are as active and selective to formaldehyde as the industrial catalyst at high methanol conversion.

While various alterations and permutations of the invention are possible, the invention is to be limited only by the following claims and equivalents.

TABLE I

Methanol Oxidation Tunover Frequencies of Pure Compounds and Mixtures Prepared by Different Synthesis Methods

| | SBET (m$^2$/g) | Synthesis | TOF(308° C.) (sec$^{-1}$)$^a$ |
|---|---|---|---|
| $MoO_3$ | 5.0 | (Thermal Decomposition) | 5.3 |
| $Fe_2O_3$ | 21.4 | (Commercial) | 26.9 |
| NiO | 34.4 | (Thermal Decomposition) | 53.1 |
| $Fe_2(MoO_4)_3$ (1.5)$^b$ | 9.6 | (Inorganic Coprecipitation) | 1.1 |
| $Fe_2(MoO_4)_3$ (1.5) | 1.5 | (Organic Coprecipitation) | 1.8 |
| $Fe_2(MoO_4)_3$ (1.1) | 3.9 | (Inorganic Coprecipitation) | 2.2 |
| $MoO_3/Fe_2(MoO_4)_3$ (2.2) | 3.0 | (Inorganic Coprecipitation) | 15.8 |
| $MoO_3 + /Fe_2(MoO_4)_3$ (2.2) | 3.5 | (Mechanical Mixture) | 14.8 |
| $MoO_3/Fe_2(MoO_4)_3$ (3.97) | 2.6 | (Mechanical Mixture) | 35.1 |
| $MoO_3 + Fe_2O_3$ (2.2) | 5.7 | (Mechanical Mixture) | 14.5 |
| $MoO_3 + NiO$ (2.2) | — | (Mechanical Mixture) | 4.2 |
| Industrial Catalyst | 7.8 | (Coprecipitation) | 29.6 |

$^a$The activity of the mixtures were obtained at 300° C. and extrapolated to 380° C.
$^b$(Mo/Fe molar ratio)

TABLE II

Methanol Oxidation Selectivities of Pure Compounds and Mixtures

| | Selectivity % | | | |
|---|---|---|---|---|
| Sample | HCHO | DME | DMM | Others |
| $MoO_3$ (Thermal Decomposition) | 84.1 | 12.0 | 3.9 | — |
| $Fe_2O_3$ (Commercial) | 57.9 | 36.4 | 1.2 | 4.5 |
| NiO (Thermal Decomposition) | 21.3 | — | — | 72.7 |
| $Fe_2(MoO_4)_3$ (1.5)$^a$ (Inorganic Coprecipitation) | 56.1 | 43.8 | — | — |
| $Fe_2(MoO_4)_3$ (1.5) (Organic Coprecipitation) | 58.2 | 41.9 | — | — |
| $Fe_2(MoO_4)_3$ (1.1) (Inorganic Coprecipitation) | 64.9 | 35.1 | — | — |
| $MoO_3/Fe_2(MoO_4)_3$ (2.2) (Inorganic Coprecipitation) | 85.3 | 11.7 | 3.2 | — |
| $MoO_3 + /(MoO_4)_3$ (2.2) (Mechanical Mixture) | 85.3 | 11.7 | 3.0 | — |
| $MoO_3/Fe_2(MoO_4)_3$ (3.97) (Mechanical Mixture) | 85.1 | 11.7 | 3.2 | — |
| $MoO_3 + FeO_3$ (2.2) (Mechanical Mixture) | 88.2 | 8.6 | 3.2 | — |
| $MoO_3 + NiO$ (2.2) (Mechanical Mixture) | 80.9 | 16.5 | 2.6 | — |
| Industrial Catalyst (Coprecipitation) | 93.0 | 7.0 | 2.0 | — |

$^a$(Mo/Fe molar ratio)

TABLE III

Activity of Mechanical Mixtures at High Methanol Conversions

| | | Selectivity % | | |
|---|---|---|---|---|
| Sample | Conversion % | HCHO | DME | Others |
| Sample C (Industrial) | 100.0 | 85.9 | 1.1 | CO, Unknown |
| $MoO_3/Fe_2(MoO_4)_3$ (2.2)$^a$ | 92.4 | 84.5 | 2.7 | CO, Unknown |
| $MoO_3/Fe_2(MoO_4)_3$ (3.97) | 100.0 | 81.7 | 2.8 | CO, Unknown |
| $MoO_3 + /Fe_2(MoO_4)_3$ (2.2) | 98.4 | 84.3 | 2.2 | CO, Unknown |

$^a$(Mo/Fe molar ratio)
Temperature = 380° C. (data obtained at this temperature)

We claim:

1. A method for forming catalytically active metal-molybdate surfaces effective for methanol oxidation to formaldehyde comprising the steps of:
   forming a fixed bed of solids comprising a first particulate source of metal oxide and a second particulate source of molybdenum oxide, said first particulate source of metal oxide being different from said second particulate source of molybdenum oxide; and
   passing a reactant stream containing methanol and oxygen through said fixed bed at conditions suitable for conversion of methanol to formaldehyde wherein catalytically active metal-molybdate is formed within said fixed bed.

2. A method according to claim 1 wherein said first particulate source of metal oxide is selected from a group consisting of oxides of iron, lead, cadmium, zinc, bismuth, sodium, manganese, gadolinium, magnesium, copper, cobalt, tellurium, aluminum, chromium, nickel, and combinations thereof.

3. A method according to claim 1 wherein said catalytically active metal-molybdate formed within said fixed bed is $Fe_2(MoO_4)_3/MoO_3$, $PbMoO_4$, $CaMoO_4$, $Bi_2Mo_2O_9$, $Bi_3(FeO_4)(MoO_4)_3$, $Na_2MoO_4$, $Na_2Mo_2O_7$, $MnMoO_4$, $Gd_2(MoO_4)_3$, $MgMoO_4$, $CuMoO_4$, $CoMoO_4$, $Te_2MoO_7$, $Al_2(MoO_4)_3$, $Cr_2(MoO_4)_3$, $NiMoO_4$, or $ZnMoO_4$.

4. A method for forming catalytically active iron-molybdate surfaces effective for methanol oxidation to formaldehyde comprising the steps of:
   forming a fixed bed of solids comprising a first particulate source of iron oxide and a second particulate source of molybdenum oxide, said first particulate source of iron oxide being different from said second particulate source of molybdenum oxide; and
   passing a reactant stream containing methanol and oxygen through said fixed bed at conditions suitable for conversion of methanol to formaldehyde wherein catalytically active $Fe_2(MoO_4)_3/MoO_3$ is formed within said fixed bed.

5. A method according to claim 4 wherein said conditions comprise a temperature within the range from about 150°–500° C.

6. A method according to claim 4 wherein said particulate source of iron comprises ferric oxide.

7. A method according to claim 4 wherein said particulate source of molybdenum oxide comprises molybdenum trioxide.

* * * * *

UNITED STATES PATENT AND TRADEMARK OFFICE
CERTIFICATE OF CORRECTION

PATENT NO. : 6,331,503 B1
DATED : December 18, 2001
INVENTOR(S) : Israel E. Wachs et al.

It is certified that error appears in the above-identified patent and that said Letters Patent is hereby corrected as shown below:

Columns 3 and 4,
Table I, "TOF(308°C)" has been replaced with -- TOF(380°C) --.
"SBET" has been replaced with -- $S_{BET}$ --.

Column 4,
Line 11, Table I, "$MoO_3/Fe_2(MoO_4)_3$ (2.2)" has been replaced with -- $MoO_3/Fe_2(MoO_4)_3$ (2.2) --.
Line 42, Table II, "$MoO_3$ + /$(MoO_4)_3$ (2.2) (Mechanical Mixture)" has been replaced with -- $MoO_3$ + /$Fe_2(MoO_4)_3$ (2.2) (Mechanical Mixture) --.
Line 45, Table II, "$MoO_3$ + $FeO_3$ (2.2) (Mechanical Mixture)" has been replaced with -- $MoO_3$ + $Fe_2O_3$ (2.2) (Mechanical Mixture) --.

Signed and Sealed this

Nineteenth Day of March, 2002

Attest:

Attesting Officer

JAMES E. ROGAN
Director of the United States Patent and Trademark Office